United States Patent [19]

Johnson

[11] 4,397,841
[45] Aug. 9, 1983

[54] PRODUCTION OF BLOOD COAGULATION FACTOR VIII:C

[75] Inventor: John H. Johnson, Kirkwood, Mo.

[73] Assignee: Monsanto Company, St. Louis, Mo.

[21] Appl. No.: 392,929

[22] Filed: Jun. 28, 1982

[51] Int. Cl.³ ............................................. A61K 35/14
[52] U.S. Cl. ..................................................... 424/101
[58] Field of Search ............................ 424/101; 5/451

[56] References Cited

U.S. PATENT DOCUMENTS

| Re. 29,698 | 7/1978 | Fekete et al. | 260/112 B |
|---|---|---|---|
| 3,555,001 | 1/1971 | Wallis et al. | 260/112 |
| 4,157,431 | 6/1979 | Fields et al. | 526/15 |
| 4,203,891 | 5/1980 | Rock | 260/112 B |
| 4,278,594 | 7/1981 | Amrani | 260/112 B |
| 4,289,691 | 9/1981 | Rock et al. | 260/112 B |
| 4,348,315 | 9/1982 | Blomback | 424/101 |
| 4,361,509 | 11/1982 | Zimmerman | 424/101 |

OTHER PUBLICATIONS

A. J. Johnson et al., *J. Lab. Clin. Med.* 92(a), 194–210 (1978).
A. J. Johnson et al., *Thromb. Diath. Haemorrh.* 34, N2, 589 (1975).

*Primary Examiner*—Sam Rosen
*Attorney, Agent, or Firm*—Scott J. Meyer; James W. Williams, Jr.

[57] ABSTRACT

A concentrate of blood coagulation Factor VIII:C is obtained in high yield by fractionation of blood plasma with a sequence of adsorption steps employing two different water-insoluble, cross-linked polyelectrolyte copolymers, each in the presence of exogenous heparin.

9 Claims, No Drawings

PRODUCTION OF BLOOD COAGULATION FACTOR VIII:C

BACKGROUND OF THE INVENTION

This invention relates to blood fractionation and more particularly to the production of blood coagulation Factor VIII:C.

The process of blood coagulation is a complicated physiological activity that involves interactions of numerous substances found in normal whole blood. It is known that certain factors associated with the blood coagulation mechanism are seriously deficient in certain individuals. Thus, in those patients suffering from classical hemophilia, antihemophilic factor A (AHF, Factor VIII) is deficient. In those patients suffering from hemophilia B, plasma thromboplastin component (PTC, Factor IX) is missing from the blood. A small percentage of hemophiliacs also are lacking in the so-called Von Willebrand Factor which is an integral component of Factor VIII.

It is now generally recognized that plasma Factor VIII is a complex of two components that have distinct functions, biochemical and immunological properties, and genetic control. One component of the Factor VIII complex has antihemophilic factor procoagulant activity and is usually designated Factor VIII:C. The other, larger component comprises the majority of the protein mass, interacts with platelets in a way that promotes primary hemostasis and is usually designated Factor VIIIR (ristocetin cofactor or Von Willebrand antigen).

Patients with Factor VIII:C deficiency transmitted by X-chromosome inheritance (hemophilia A patients) have normal Factor VIIIR synthesis and function. Such patients thus do not require exogenous administration of Factor VIIIR for maintenance of hemostasis, and a concentrate of Factor VIII:C free of Factor VIIIR would be satisfactory and in some cases even preferable.

Further background information on the structure and function of the Factor VIII complex and its two components can be had by reference to the three recent review articles by, respectively, Hoyer, *J. Amer. Soc. of Hematol.* 58 (1), 1–13 (1981); Harris et al, *Biochim. Biophys. Acta* 668, 456–470 (1981); and Fulcher et al, *Proc. Natl. Acad. Sci. USA* 79, 1648–1652 (1982).

The clinical importance of Factor VIII concentrates and the critical need for adequate supplies thereof has provided motivation to develop improved methods for the production of such blood fractions. As alternatives to the conventional Cohn alcohol process of blood fractionation which must be conducted at cold temperatures, various other methods have been developed which employ fractionating agents that can be used at normal room temperature (ambient temperature). One such method employs the polymer polyethylene glycol (PEG) as described, e.g., in U.S. Pat. Nos. 3,631,018; 3,652,530; and 3,682,881. However, the methodology described in these patents additionally employs a cryoprecipitation step which necessitates the use of cold temperature facilities and also results in a loss of a substantial amount of the Factor VIII activity.

Addition of heparin at various stages of these PEG/cryoprecipitation fractionation processes to increase the yield of Factor VIII has been suggested in U.S. Pat. Nos. 3,803,115; Re. 29,698; 4,203,891; and 4,289,691. In the first two of these patents the heparin is added after the cryoprecipitation step whereas in the latter two patents it is added before the cryoprecipitation step.

The aforesaid prior art methods for the production of Factor VIII by use of polyethylene glycol, cryoprecipitation and heparin are not reported to provide a Factor VIII:C concentrate as distinguished from the Factor VIII complex. However, heparin has been suggested for addition to plasma in fractionation methodology to separate AHF, von Willebrand's ristocetin cofactor and fibronectin by cold temperature precipitation and chromatography according to U.S. Pat. Nos. 4,210,580 and 4,278,594.

Another method of improvement over the conventional Cohn alcohol blood fractionation process employs water-insoluble, cross-linked polyelectrolyte copolymer adsorbents as described, e.g., in U.S. Pat. Nos. 3,554,985; 3,555,001; 4,118,554; and 4,157,431; and by A. J. Johnson, et al., *J. Lab. Clin. Med.* 92 (a), 194–210 (1978). These polymeric materials have been employed in combination with other agents such as dithiothreitol, Sepharose CL-4B and Sephadex G-100 to produce a concentrate of Factor VIII:C substantially free of Factor VIIIR. Harris et al., *Biochim. Biophys. Acta* 668, 456–470 (1981).

DESCRIPTION OF THE INVENTION

It has now been found that a concentrate of Factor VIII:C can be fractionated from blood plasma in high yield at ambient temperature with a sequence of adsorption steps employing, at differing concentrations and pH levels, two different water-insoluble, cross-linked polyelectrolyte copolymers, each in the presence of exogenous heparin. In accordance with the present invention, such concentrate of Factor VIII:C is obtained by a method which comprises:

(a) admixing blood plasma or a concentrate thereof at pH of from about 7.0 to about 8.5 with from about 0.01% to about 0.1% by weight of water-insoluble, polyelectrolyte copolymer of ethylene and maleic anhydride cross-linked with from about 3 mole % to about 10 mole % of loweralkyliminobis(loweralkylamine) and containing from about 90 mole % to about 100 mole % of pendant diloweralkylaminoloweralkylimide functional groups, said admixing in the presence of exogenous heparin, (b) separating the supernatant from the resulting adsorbed plasma fraction, (c) admixing said supernatant at pH of from about 5.5 to about 6.5 with from about 1% to about 10% by weight of water-insoluble, polyelectrolyte copolymer of ethylene and maleic anhydride cross-linked with from about 3 mole % to about 10 mole % of loweralkyliminobis(loweralkylamine), containing from about 3 mole % to about 7 mole % of pendant diloweralkylaminoloweralkylimide functional groups, and further characterized in that substantially all the remaining free carboxyl or anhydride sites are blocked with alkoxyalkylamine, said admixing in the presence of exogenous heparin, (d) separating the resulting adsorbed plasma fraction from the supernatant and recovering therefrom a concentrate of Factor VIII:C by elution from the adsorbent, and (e) wherein said alkyl and alkoxy have from about one to about four carbon atoms.

The preferred level of heparin used herein ranges from about 0.01 to about 2 units per ml of plasma and most preferably from about 0.1 to about one unit per ml of plasma. The preferred concentration of polyelectrolyte used herein ranges from about 0.03% to about 0.04% in adsorption step (a) and from about 5% to about 6% in adsorption step (c).

As used herein, one unit of heparin is defined to mean one U.S.P. (United States Pharmacopoeia) unit. The U.S.P. unit of heparin is that quantity which will prevent 1.0 ml of citrated sheep plasma from clotting for one hour after the addition of 0.2 ml of a 1:100 $CaCl_2$ solution. Heparin is generally obtained by isolation from mammalian tissues containing mast cells such as the liver and lung. As used herein, the term "heparin" also is meant to include the pharmaceutically acceptable water soluble salts thereof, e.g., the sodium salt. Suitable examples of commercially available heparin sodium products are Lipo-Hepin ® (Riker Laboratories), Liquaemin ® Sodium (Organon), and Panheprin ® (Abbott Laboratories).

The anticoagulant properties of heparin have been known since Howell's discovery in 1922. *Amer. J. Physol.* 63, 434–435 (1922). It is now known that heparin acts as an anticoagulant indirectly by means of a plasma cofactor. The heparin cofactor, Antithrombin III, is an $a_2$-globulin and a serine protease inhibitor that prevents the serine protease from inactivating the clotting factors. Antithrombin III forms complexes with thrombin and, as a result, both proteins are inactivated. Heparin markedly accelerates the velocity but not the extent of this reaction. Low concentrations of heparin increase the activity of Antithrombin III which forms the basis of heparin administration as a therapeutic.

Heparin addition to blood for collection and preservation of donor blood is well known as seen, e.g., from Button et al., *Transfusion* 3, 37–40 (1963). It is also known that heparin can be added to stored plasma to prevent inactivation of Factor VIII by thrombin. Rizza et al., *Nature* (Lond.) 180, 143 (1957) and Stibbe et al., *Thromb. Diath. Haemorrh.* 27, 43–58 (1972). However, donor blood is now generally collected in ACD, CPD or CPD plus adenine (CPDA-1) anticoagulants instead of heparin for purposes of erythrocyte survival. Moreover, heparinized blood is unsuitable for various tests, e.g., tests that involve complement, isoagglutinins, or erythrocyte fragility. Therefore, blood to be used for such tests would require removal or neutralization of heparin anticoagulants.

Although heparin has been used heretofore in connection with blood fractionation methods which employ polyelectrolyte polymers of the type used in the present invention, the heparin was added to the eluate from the adsorbent which was then fractionated with polyethylene glycol to obtain Factors II, VII, IX and X (prothrombin complex). A. J. Johnson et al., *J. Lab. Clin. Med.* 92 (a), 194–210 (1978). Heparin was used in the production of the prothrombin complex factors by polyethylene glycol precipitation, as reported by A. J. Johnson et al., for provision of a heparin-activated Antithrombin III to inhibit activated clotting factors. See *Thromb. Diath. Haemorrh.* 34, N2, 589 (1975). There has been no suggestion in the prior art to use heparin in a blood fractionation sequence with the polyelectrolyte polymers to obtain high yields of a Factor VIII:C concentrate as defined herein.

The polyelectrolyte polymers used in combination with the heparin in accordance with the present invention are known compounds which can be made according to methods described in U.S. Pat. Nos. 3,554,985; 3,555,001; 4,118,554; and 4,157,431. For example, the base copolymer of ethylene and maleic anhydride (EMA) can be prepared by reacting ethylene and maleic anhydride in the presence of peroxide catalyst in a suitable solvent medium. The copolymer will preferably contain substantially equimolar quantities of the ethylene residue and the anhydride residue.

The base EMA copolymer can be reacted with a loweralkyliminobis(loweralkylamine) which has two primary amine groups and leads to a cross-linked EMA copolymer. The EMA copolymer should be reacted with from about 3 mole % to about 10 mole % of the cross-linking agent. The desired pendant diloweralkylaminoloweralkylimide functional groups can then be incorporated into the cross-linked copolymer to a level of at least about 3 mole % by reaction of diloweralkylaminoloweralkylamine with part or all of the remaining free anhydride groups of the EMA copolymer. From about 90 mole % to about 100 mole % of the diloweralkylaminoloweralkylamine preferably is used for preparing the polyelectrolyte polymeric adsorbent employed in step (a) of the present invention whereas from about 3 mole % to about 7 mole % preferably is used for preparing the adsorbent employed in the subsequent step (c) of the present invention. In the case of the latter polyelectrolyte polymeric adsorbent, substantially all the remaining free carboxyl or anhydride sites are blocked with alkoxyalkylamine as disclosed in U.S. Pat. No. 4,157,431.

The polyelectrolyte polymeric materials used in the present invention also can be prepared by methods which employ the aggregation step disclosed in U.S. Pat. No. 4,118,554.

A preferred diloweralkylaminoloweralkylimide functional group is dimethylaminopropylimide, a preferred cross-linking agent is methyliminobispropylamine, and a preferred alkoxyalkylamine blocking agent is methoxypropylamine.

It will be appreciated that the foregoing methods of production of the polyelectrolyte polymeric adsorbents are for illustrative purposes only and that the method of fractionating blood with these materials in accordance with the invention is not limited to any particular method of their preparation.

It is presently believed to be important to one aspect of the present invention that the exogenous heparin be employed during both adsorption steps with the polyelectrolyte polymers since the first adsorption step may also adsorb a substantial amount of the heparin from the plasma medium when exogenously added to that medium. Generally, the amount of heparin to add prior to the second adsorption step will be equivalent to the amount removed by the first adsorption step. The heparin can be added initially during the blood collection process or it can be added to blood collected in other anti-coagulants such as ACD, CPD or CPDA.

In accordance with another aspect of the invention, the heparin can also be incorporated directly with the polyelectrolyte polymer before treatment of the blood with the polymer. In the latter case the heparin also can be bound to the polymer by ionic bonds to form a polyelectrolyte polymer/heparin complex. The polyelectrolyte polymer/heparin complex can be conveniently formed by admixing the heparin and the polymer in aqueous suspension followed by separating the resulting complex and drying.

The starting blood plasma material can be whole blood plasma or a concentrate thereof known to contain Factor VIII:C, for example, a cryoprecipitate concentrate.

The adsorption steps of the blood fractionation process are carried out in aqueous suspension, preferably in physiological saline solution. Appropriate pH adjustments to the desired basic or acidic levels can be made by treatment of the plasma medium with, respectively, NaOH to raise the pH to a range of from about 7.0 to about 8.5 in adsorption step (a) of the process, and with HCl, acetic acid or preferably citric acid to lower the pH to a range of from about 5.5 to about 6.5 in adsorption step (c) of the process.

Separation of the adsorbed plasma fractions from the respective supernatants after each adsorption step can be made by filtration, centrifugation and the like separation procedures. Elution of the desired Factor VIII:C concentrate can be had by washing the final adsorbent with from about one to about three molar NaCl, preferably from about 1.5 to about 1.8 molar NaCl, and with other such physiologically acceptable eluants.

The Factor VIII:C concentrate can be converted to a physiologically suitable, sterile solid form by employing a partial desalination and concentration (e.g., such as membrane ultrafiltration), sterile filtration (e.g., such as by filtration through a semiporous membrane having a pore size of about 4 microns) and subsequent lyophilization.

Factor VIII:C activity in the final recovered product can be determined by conventional one-stage or two-stage assay methods which employ measurement of activated partial thromboplastin time (PTT). In these tests, the addition of partial thromboplastin to a test plasma will measure deficiencies of various plasma factors. The well-known one-stage prothrombin time test developed by Quick is preferred. For background information on the one-stage assay tests see Quick, "Hemorrhagic Diseases", Lea & Febiger, Philadelphia, Pa., 1957; Langdell et al., *J. Lab. Clin. Med.* 41, 637 (1953); and Hardisty et al.; *Thromb. Diath. Haemorrh.* 7, 215 (1962).

Presence of Factor VIIIR activity in the final product can be determined by aggregation when exposed to the antibiotic substance ristocetin and measurement by immunoelectrophoresis or radioimmunoassay. Suitable such assay procedures are described by Harris et al., *Biochim. Biophys. Acta* 668, 456–470 (1981), and by Fulcher et al., *Proc. Natl Acad. Sci. USA* 79, 1648–1652 (1982).

Although human blood is particularly described herein, it will be appreciated that other animal blood such as, e.g., bovine, porcine, equine and ovine can similarly be fractionated in accordance with the present invention.

The following examples will further illustrate the invention although it will be understood that the invention is not limited to these specific examples or the details recited therein.

EXAMPLE 1

Human donor blood was drawn into plastic blood collection bags containing CPDA-1 anticoagulant. Plasma was separated from the blood serum by refrigerated centrifugation within 4 hours of collection. Forty units of plasma were pooled and aliquoted (200 ml) into 300 ml unit transfer bags which were then frozen and stored at $-20°$ C.

The fresh frozen plasma was fractionated at ambient temperature in a sequence of adsorption steps employing two different water-insoluble, cross-linked polyelectrolyte resins in the presence of exogenous heparin. These resins were copolymers of substantially equimolar amounts of ethylene and maleic anhydride, cross-linked with 5 mole % of methyliminobispropylamine, and containing pendant dimethylaminopropylimide pendant groups. The first resin, Resin A, contained 90 mole % of these pendant groups, whereas the second resin, Resin B, contained 5 mole % of said pendant groups. In Resin B all the free carboxyl or anhydride groups were further blocked with methoxypropylamine.

Prior to use, Resin B was preconditioned as follows:

Twelve grams of the resin were disposed in 200 ml of 0.154 M NaCl containing 0.1% bovine serum albumin (BSA). (Human serum albumin also can be used instead of BSA). The pH was adjusted to 4.0 with 1.0 M citric acid to facilitate dispersion (about 3–5 minutes with stirring). The suspension was filtered and the filtrate discarded. The wet resin cake was again dispersed in 200 ml of the NaCl/BSA solution. The pH was adjusted while stirring to 5.8 with 1.0 M NaOH; stirring was continued for an additional 10 minutes. The suspension was filtered and the wet cake reserved for use in the subsequent fractionation.

All eluant and wash solutions used in the fractionation also contained 0.1% BSA to minimize binding of the desired proteins to surfaces and to further act as a stabilizer for Factor VIII:C.

Porcine heparin, sodium salt, was employed in the fractionation by solution in physiological saline (0.9 NaCl) to provide a solution containing about 200 units/ml.

The fractionation process was carried out as follows:

One bag (i.e. 200 ml) of the fresh frozen plasma was rapidly thawed by placing in a stirred water bath at 37° C. For the tests incorporating heparin, one milliliter of heparin solution (i.e. 200 units) was added to the thawed plasma in a beaker and the mixture stirred for 3–5 minutes. A sample of plasma was taken for the coagulation assay. Volume and time were noted. Control runs were made without addition of heparin to the plasma but were otherwise identical to the test runs.

Resin A (70 mg) was added to the plasma (or heparinized plasma), the pH was adjusted to 8.0 with 1 M NaOH and maintained at this pH with stirring for 20 minutes. It was then filtered; the filtrate contained most of the Factor VIII:C activity. The wet resin cake was resuspended in 20 ml of distilled water, stirred for 5 minutes, filtered, and the two filtrates were then combined and sampled for assay of Factor VIII:C activity. The volume was recorded to permit calculation of total coagulation units present.

The pre-conditioned resin B (12 g) was then added to the filtrate (or heparinized filtrate), the pH adjusted to 5.8 with 1 M citric acid and the suspension was stirred for 20 minutes while maintaining the pH at 5.8. It was then filtered and the filter cake washed with 200 ml of 0.002 M NaCl. The combined filtrates were retained for recovery of albumin and gamma globulin plasma fractions. The filter cake was dispersed in 200 ml of 0.3 M NaCl, the pH adjusted to 5.8 and the suspension was stirred for 5 minutes. The suspension was again filtered, washed on the filter with another 200 ml of 0.3 M NaCl and the filtrate was discarded.

The filter cake was then dispersed in 200 ml of eluant solution which contained sodium chloride (1.5 M), lysine (0.1 M) as a stabilizer, and bovine serum albumin (0.1%). The pH was adjusted to 6.0 and the suspension was stirred for 20 minutes. The suspension was filtered, the cake optionally washed with approximately 20 ml of eluant solution, the volume of combined filtrates noted and a sample was taken for coagulation assay as reported in Table 1, below.

The filtrates, containing 40–70% of the original Factor VIII:C coagulation activity in purified form, can then be processed to achieve further concentration and partial desalination. This can be achieved, for example, by employing a Millipore Pellicon ® Cassette filtration system or an Amicon DH 4 hollow fiber concentrator system, with a semi-permeable polysulfone fiber membrane having an appropriate molecular weight cutoff for retention of the desired molecules. The concentrated solution can then be freeze dried and packaged for storage. These further concentration and processing steps were not, however, carried out in this specific Example 1.

The following Table 1 presents results of several fractionation runs employing pooled CPDA-stabilized plasma and the process described above. These results demonstrate the beneficial effects of heparin addition to the pooled plasma in combination with polyelectrolyte polymer fractionation. They illustrate a reproducible improvement in recovery of Factor VIII:C coagulation activity both after the Resin A treatment which removed Factor IX complex and in overall activity recovery (based on the level in the original plasma) after adsorption and elution from the Resin B.

The Factor VIII:C determination was made by a conventional one-stage PTT assay system on an MLA Electra Coagulation Timer (Medical Laboratory Automation, Inc.). This instrument employs optical sensing to indicate commencement of the clotting process. It measures the second derivative of the coagulation rate (i.e., the rate of change of the coagulation rate). The assay was made with a reagent kit and procedure commercially supplied by Dade Diagnostics, Inc., which includes Factor VIII deficient plasma and ellagic acid activator as described in U.S. Pat. No. 3,486,981. Coagulation times were determined for serial dilutions of the test samples (the fractionated samples) and results were expressed as percent of recovery of Factor VIII:C activity based on the level in the original pooled plasma sample. In these runs, the pooled plasma was assumed to contain 1 unit/ml of Factor VIII:C coagulation activity. Therefore, each of the runs was initiated with a total of 200 coagulation units. The cumulative unit and percent recovery of activity after each resin treatment is reported.

TABLE 1

| Run No. | Units Eluted from Resin A | Recovery from Resin A (%) | Units Eluted from Resin B | Recovery from Resin B (%)* |
|---|---|---|---|---|
| CONTROL RUNS - NO HEPARIN ADDED | | | | |
| 1 | 145 | 72.5 | 88 | 44.0 |
| 2 | 137 | 68.5 | 76 | 38.0 |
| 3 | 106 | 53.0 | 41 | 20.5 |
| 4 | 144 | 72.0 | 84 | 42.0 |
| 5 | 105 | 52.5 | 93 | 46.5 |
| Ave (S.D.) | 127 ± 20 | 63.7 ± 10.1 | 76.0 ± 21.0 | 38.2 ± 10.4 |
| HEPARIN TREATMENT (1.03 UNITS/ML) | | | | |
| 6 | 171 | 85.5 | 118 | 59.0 |
| 7 | 190 | 95.0 | 120 | 60.0 |
| 8 | 166 | 83.0 | 112 | 56.0 |
| 9 | 164 | 82.0 | 109 | 54.5 |
| 10 | 204 | 102.0 | 139 | 69.5 |
| Ave (S.D.) | 188 ± 27.0 | 93.9 ± 13.5 | 120 ± 12.0 | 59.8 ± 5.9 |

*Based on initial plasma level

EXAMPLE 2

Additional fractionation runs were made as in Example 1, above, except that three different concentrations of heparin (1.0 unit/ml; 0.5 unit/ml; and 0.1 unit/ml) were added to the initial plasma in step (a) prior to adsorption with Resin A and also to the effluent (filtrate) in step (c) prior to adsorption with Resin B.

The following Table 2 presents the results of these fractionation runs in terms of percent recovery of Factor VIII:C activity in which the original pooled plasma was assumed to contain 1 unit/ml.

TABLE 2

| | Amount Heparin Added | | |
|---|---|---|---|
| | 1.0 unit/ml | 0.5 unit/ml* | 0.1 unit/ml |
| Recovery from Resin A (%) | 91 ± 6 | 81 | 96 ± 14 |
| Cumulative Recovery from Resin B (%) | 53 ± 17 | 48 | 53 ± 5 |

*One run only

EXAMPLE 3

In this example, polyelectrolyte polymer/heparin complexes were initially prepared by contacting the respective Resin A and Resin B products of Example 1, above, with aqueous solutions of sodium heparin and drying the resulting complexes. These resin/heparin complexes were then used to fractionate blood according to the procedure of Example 1 without further exogenous addition of heparin solution.

Initially, porcine heparin, sodium salt (1003 units dissolved in 50 ml of water) was added to each of:

(A) 300 mg of Resin A suspended in 100 ml of water, and (B) 50 g of Resin B suspended in 200 ml of water.

In each case, stirring was maintained at ordinary room temperature (ca. 22°–25° C.) for about one hour. The resin/heparin complexes were isolated by filtration on Whatman #54 cellulosic filter paper (98% retention efficiency at 20–25 microns according to the manufacturer) followed by washing three times with 100 ml portions of water to remove any unbound heparin. The resin/heparin complexes were then dried prior to employment in the blood fractionation process.

Plasma was fractionated substantially as described in Example 1 except that the resin/heparin complexes were used in place of the corresponding resins and further exogenous addition of heparin was omitted.

In this example, recovery of Factor VIII:C coagulation activity after the Resin A/heparin complex treatment was quantitative within the limits of ordinary experimental error (117%). The overall recovery after adsorption and elution from the Resin B/heparin complex was 78.4% of the level in the original plasma in this particular example.

In the foregoing Examples 1-3, Resin A was made substantially according to methods with reactants and molar proportions as described in Example 1 of U.S. Pat. Nos. 4,097,473 and 4,118,554 and Example 12 of U.S. Pat. No. 4,157,431. Resin B was made substantially according to methods with reactants and molar proportions as described in Example 1 of U.S. Pat. No. 4,157,431.

EXAMPLE 4

Substantially similar results as obtained in Examples 1-3, above, are obtained when diethylaminoethylamine is substituted for an equivalent amount of dimethylaminopropylamine, and/or when ethyliminobisethylamine is substituted for an equivalent amount of methyliminobispropylamine, and/or when ethoxyethylamine is substituted for an equivalent amount of methoxypropylamine in said Examples 1-3.

Various other examples will be apparent to the person skilled in the art after reading the present disclosure without departing from the spirit and scope of the invention and it is intended that all such other examples be included within the scope of the appended claims.

What is claimed is:

1. A method for the preparation of a concentrate of Factor VIII:C from blood plasma which comprises
    (a) admixing said blood plasma or a concentrate thereof at pH of from about 7.0 to about 8.5 with from about 0.01% to about 0.1% by weight of water-insoluble, polyelectrolyte copolymer of ethylene and maleic anhydride cross-linked with from about 3 mole % to about 10 mole % of loweralkyliminobis(loweralkylamine) and containing from about 90 mole % to about 100 mole % of pendant diloweralkylaminoloweralkylimide functional groups, said admixing in the presence of exogenous heparin,
    (b) separating the supernatant from the resulting adsorbed plasma fraction,
    (c) admixing said supernatant at pH of from about 5.5 to about 6.5 with from about 1% to about 10% by weight of water-insoluble, polyelectrolyte copolymer of ethylene and maleic anhydride cross-linked with from about 3 mole % to about 10 mole % of loweralkyliminobis(loweralkylamine), containing from about 3 mole % to about 7 mole % of pendant diloweralkylaminoloweralkylimide functional groups, and further characterized in that substantially all the remaining free carboxyl or anhydride sites are blocked with alkoxyalkylamine, said admixing in the presence of exogenous heparin,
    (d) separating the resulting adsorbed plasma fraction from the supernatant and recovering therefrom a concentrate of Factor VIII:C by elution from the adsorbent, and
    (e) wherein said alkyl and alkoxy have from about one to about four carbon atoms and the exogenous heparin is present in a range of from about 0.01 to about two units per ml of plasma.

2. The method of claim 1 in which the copolymer of ethylene and maleic anhydride is cross-linked with methyliminobispropylamine and in which the pendant diloweralkylaminoloweralkylimide functional group is dimethylaminopropylimide.

3. The method of claim 1 in which the heparin level in steps (a) and (c) is from about 0.1 to about one unit per ml.

4. The method of claim 1 in which the concentration of the polyelectrolyte copolymer in step (a) is about 0.03-0.04% and in step (c) is about 5-6%.

5. The method of claim 1 in which the copolymer of ethylene and maleic anhydride is cross-linked with methyliminobispropylamine, the pendant diloweralkylaminoloweralkylimide functional group is dimethylaminopropylimide, the heparin level in steps (a) and (c) is from about 0.1 to about one unit per ml and the concentration of polyelectrolyte copolymer in step (a) is about 0.03-0.04% and in step (c) is about 5-6%.

6. The method of claim 1 in which the exogenous heparin is incorporated in solution with the blood plasma in step (a) and the supernate in step (c).

7. The method of claim 5 in which the exogenous heparin is incorporated in solution with the blood plasma in step (a) and the supernate is step (c).

8. The method of claim 1 in which the exogenous heparin is precomplexed with the polyelectrolyte copolymers used in steps (a) and (c).

9. The method of claim 5 in which the exogenous heparin is precomplexed with the polyelectrolyte copolymers used in steps (a) and (c).

* * * * *